(12) United States Patent
Williams et al.

(10) Patent No.: US 10,973,426 B2
(45) Date of Patent: *Apr. 13, 2021

(54) BASKET CATHETER WITH IMPROVED SPINE FLEXIBILITY

(71) Applicant: BIOSENSE WEBSTER (ISRAEL) LTD., Yokneam (IL)

(72) Inventors: Stuart Williams, Ontario, CA (US); Paul Tran, Irwindale, CA (US); Mario A. Solis, Rancho Cucamonga, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/813,614

(22) Filed: Mar. 9, 2020

(65) Prior Publication Data
US 2020/0205690 A1    Jul. 2, 2020

Related U.S. Application Data

(63) Continuation of application No. 16/267,271, filed on Feb. 4, 2019, now Pat. No. 10,582,871, which is a
(Continued)

(51) Int. Cl.
*A61B 5/042*       (2006.01)
*A61B 18/14*       (2006.01)
(Continued)

(52) U.S. Cl.
CPC .......... *A61B 5/0422* (2013.01); *A61B 5/6858* (2013.01); *A61B 18/1492* (2013.01);
(Continued)

(58) Field of Classification Search
CPC ... A61B 5/0422; A61B 5/6858; A61B 5/6859; A61B 2018/00267; A61B 18/1492
See application file for complete search history.

(56) References Cited

U.S. PATENT DOCUMENTS 5,345,936 A    9/1994  Pomeranz et al.
5,391,199 A    2/1995  Ben-Haim
(Continued)

FOREIGN PATENT DOCUMENTS

EP          2 921 125 A1    9/2015
WO       WO 95/02995       2/1995
(Continued)

OTHER PUBLICATIONS

European Search Report for EP Patent Application No. 15202335.4 dated May 23, 2016, 6 pages.

*Primary Examiner* — Lee S Cohen
(74) *Attorney, Agent, or Firm* — Lewis Roca Rothgerber Christie LLP

(57) ABSTRACT

A catheter with basket-shaped electrode assembly with spines configured for hyper-flexing in a predetermined, predictable manner when a compressive force acts on the assembly from either its distal end or its proximal end. At least one spine has at least one region of greater (or hyper) flexibility that allows the electrode assembly to deform, for example, compress, for absorbing and dampening excessive force that may otherwise cause damage or injury to tissue wall in contact with the assembly, without compromising the structure and stiffness of the remaining regions of the spine, including its distal and proximal regions. The one or more regions of greater flexibility in the spine allow the spine to flex into a generally V-shape configuration or a generally U-shape configuration.

20 Claims, 16 Drawing Sheets

Related U.S. Application Data continuation of application No. 15/728,401, filed on Oct. 9, 2017, now Pat. No. 10,194,818, which is a continuation of application No. 14/587,497, filed on Dec. 31, 2014, now Pat. No. 9,782,099.

(51) Int. Cl.
*A61B 5/00* (2006.01)
*A61B 18/00* (2006.01)

(52) U.S. Cl.
CPC .............. *A61B 2018/0016* (2013.01); *A61B 2018/00059* (2013.01); *A61B 2018/00267* (2013.01); *A61B 2018/00351* (2013.01); *A61B 2018/00357* (2013.01); *A61B 2018/00577* (2013.01); *A61M 2210/125* (2013.01)

(56) References Cited

U.S. PATENT DOCUMENTS

| | | |
|---|---|---|
| 5,443,489 A | 8/1995 | Ben-Haim |
| 5,465,717 A | 11/1995 | Imran et al. |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-haim |
| 5,772,590 A | 6/1998 | Webster, Jr. |
| 5,928,228 A | 7/1999 | Kordis et al. |
| 6,014,590 A | 1/2000 | Whayne et al. |
| 6,024,739 A | 2/2000 | Ponzi et al. |
| 6,064,905 A | 5/2000 | Webster, Jr. et al. |
| 6,748,255 B2 | 6/2004 | Fuimaono et al. |
| 6,973,340 B2 | 12/2005 | Fuimaono et al. |
| 7,335,196 B2 | 2/2008 | Swanson et al. |
| 8,364,236 B2 | 1/2013 | Burke et al. |
| 8,588,885 B2 | 11/2013 | Hall et al. |
| 8,644,902 B2 | 2/2014 | Kordis et al. |
| 9,204,929 B2 | 12/2015 | Solis |
| 9,782,099 B2 | 10/2017 | Williams et al. |
| 10,194,818 B2 | 2/2019 | Williams et al. |
| 10,582,871 B2 * | 3/2020 | Williams .............. A61B 5/6858 |
| 2011/0118726 A1 | 5/2011 | De La Rama et al. |
| 2012/0271140 A1 | 10/2012 | Kordis et al. |
| 2013/0172715 A1 | 7/2013 | Just et al. |
| 2014/0148674 A1 | 5/2014 | Hall et al. |
| 2014/0305699 A1 | 10/2014 | Govari |
| 2014/0309512 A1 | 10/2014 | Govari et al. |
| 2014/0324043 A1 | 10/2014 | Terwey et al. |

FOREIGN PATENT DOCUMENTS

| | | |
|---|---|---|
| WO | WO 96/05768 | 2/1996 |
| WO | WO 97/24983 | 7/1997 |
| WO | WO 98/29033 | 7/1998 |

* cited by examiner

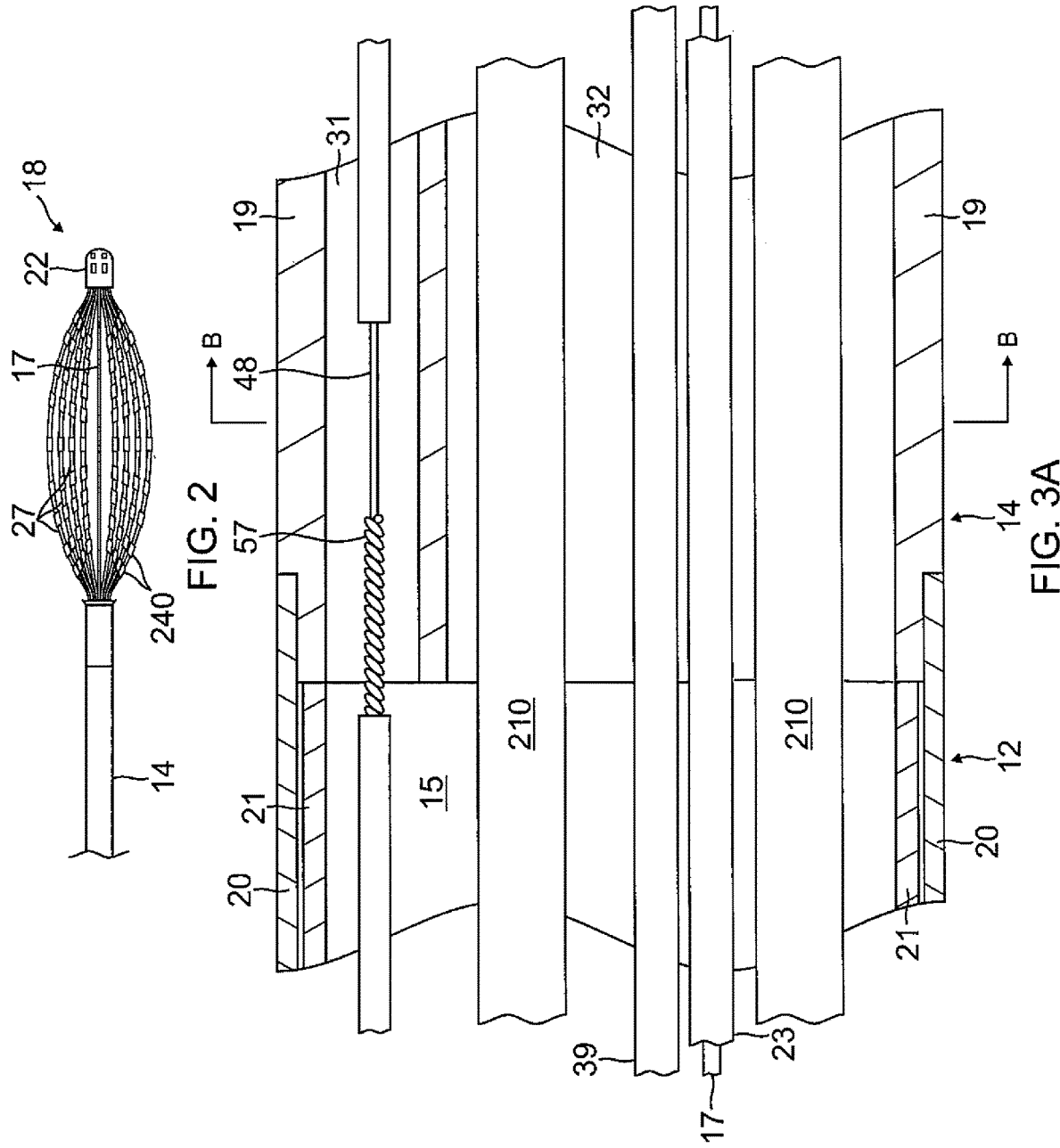

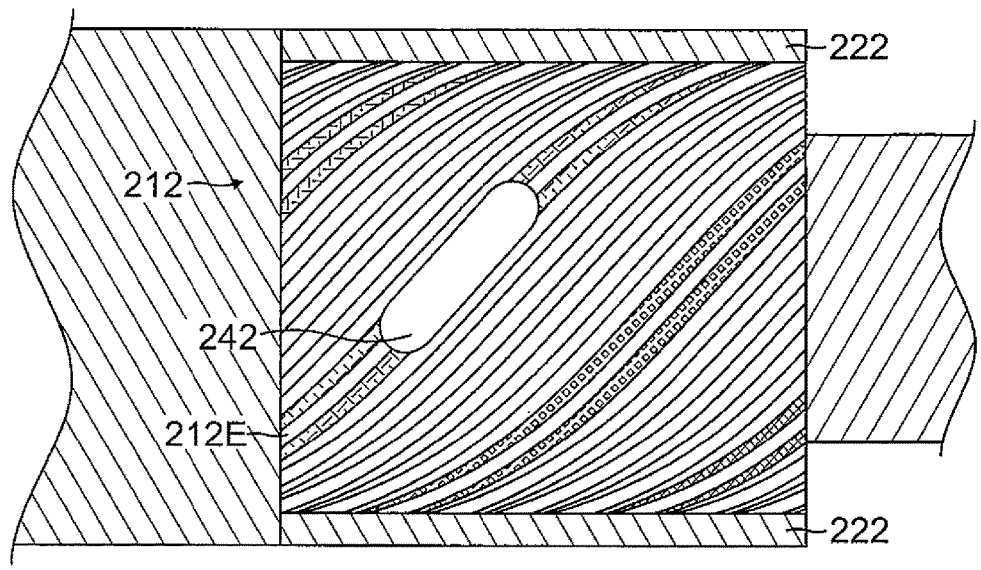
FIG. 5A
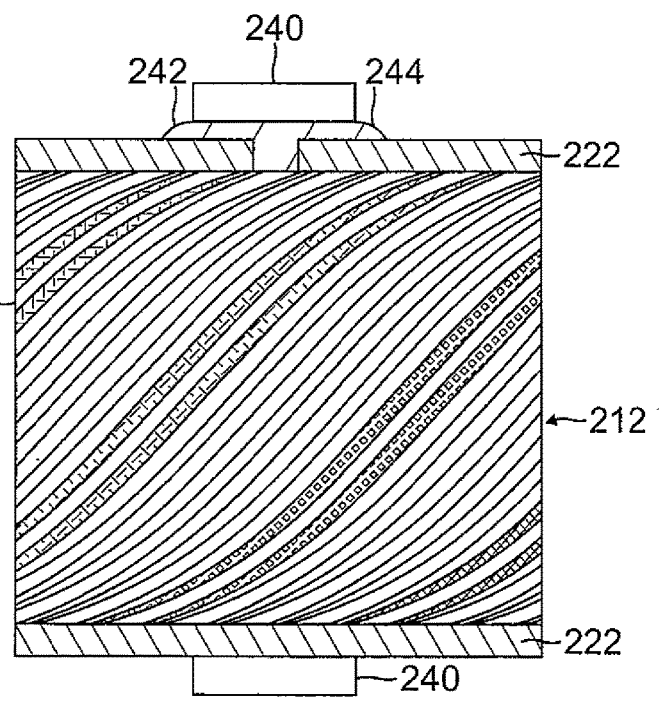
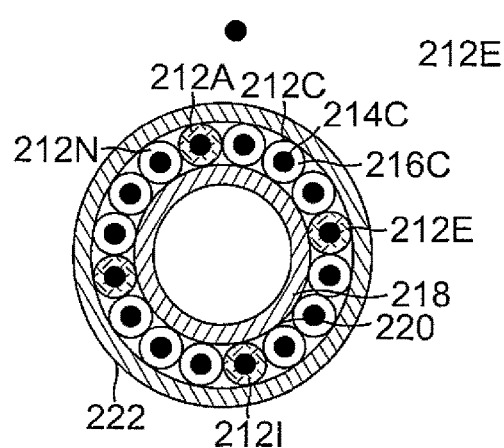
FIG. 5B
FIG. 5C

BASKET CATHETER WITH IMPROVED SPINE FLEXIBILITY

This application is a continuation of and claims priority to and the benefit of U.S. application Ser. No. 16/267,271 filed Feb. 4, 2019, now U.S. Pat. No. 10,582,871, which is a continuation of and claims priority to and the benefit of U.S. application Ser. No. 15/728,401 filed Oct. 9, 2017, issued as U.S. Pat. No. 10,194,818, which is a continuation of and claims priority to and the benefit of U.S. application Ser. No. 14/587,497 filed Dec. 31, 2014, issued U.S. Pat. No. 9,782,099, the entire contents of all of which are incorporated herein by reference.

FIELD OF INVENTION

Field of Invention

This invention relates to electrophysiologic (EP) catheters, in particular, EP catheters for mapping and/or ablation in the heart.

Background

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of both of which are incorporated herein by reference.

Basket catheters typically have an elongated catheter body and a basket-shaped electrode assembly mounted at the distal end of the catheter body. The assembly has proximal and distal ends and comprises a plurality of spines connected at their proximal and distal ends. Each spine comprises at least one electrode. The assembly has an axial elongated expander which is longitudinally movable relative to the catheter by an EP professional to vary the configuration of the basket between an expanded arrangement wherein the spines bow radially outwardly and a collapsed arrangement wherein the spines are arranged generally along the axis of the catheter body. The catheter may further comprise a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the assembly to find the positions of the at least one electrode of each spine.

A basket-shaped electrode assembly is capable of detecting in a single beat most or all of the electrical function of the left or right atrium. However, because the atria of an individual patient may vary in size and shape, it is desirable that the assembly be sufficiently versatile and steerable to conform to the particular atrium. A basket catheter with a deflectable assembly for improved maneuverability to provide better tissue contact, especially in a cavernous region of the heart, including an atrium, is described in U.S. Pat. No. 9,204,929 (corresponding to application Ser. No. 14/028,435, filed Sep. 16, 2013), the entire disclosure of which is hereby incorporated by reference.

While a deflectable basket catheter whose basket configuration can be varied by an expander enables an EP professional to adjust the basket for a better fit within any particular atrium, a basket with stiffer spines may enable better contact between the spines and the atrial wall. However, stiffer spines may increase the risk of injury and damage to the atrial wall.

Nitinol wire is often used in the construction of therapeutic and diagnostic catheter distal ends, including basket-shaped electrode assemblies. At body temperature, nitinol wire is flexible and elastic and like most metals nitinol wires deform when subjected to minimal force and return to their shape in the absence of that force. Accordingly, a 3-D distal assembly can be easily collapsed to be fed into a guiding sheath, and readily deployed in the chamber or tubular region upon removal of the guiding sheath. Because Nitinol belongs to a class of materials called Shaped Memory Alloys (SMA). These materials have interesting mechanical properties beyond flexibility and elasticity, including shape memory and superelasticity which allow nitinol to have a "memorized shape."

Nitinol has different temperature phases, including martensitic phase and austenite phase. The austenite phase is Nitinol's stronger, higher-temperature phase. Crystalline structure is simple cubic. Superelastic behavior occurs in this phase (over a 50°-60° C. temperature spread). The Martensite phase is Nitinol's weaker, lower-temperature phase. Crystalline structure is twinned. Material is easily deformed in this phase. Once deformed in martensite, it will remain deformed until heated to austenite where it will return to its pre-deformed shape, producing the "shape memory" effect. The temperature at which Nitinol starts to transform to austenite upon heating is referred to as the "As" temperature. The temperature at which Nitinol has finished transforming to austenite upon heating is referred to as the "Af" temperature.

Accordingly, it is desirable that a basket catheter have spines that are sufficiently pliable and flexible to minimize the risk of injury and damage to the atrial wall, yet provide sufficient stiffness for dependable tissue contact and electrode spacing. It is also desirable that a basket catheter have spines constructed of material with shape memory, such as nitinol, so as to employ some of its advantageous properties.

SUMMARY OF THE INVENTION

The present invention is directed to a catheter with a basket-shaped electrode assembly configured to adopt a collapsed configuration, an expanded configuration and a hyper-expanded configuration. The assembly has spines with portions of greater (hyper) flexibility, and portions of lesser flexibility by comparison, for enabling dependable tissue contact and electrode space, without increasing the risk of tissue damage. In accordance with a feature of the present invention, one or more spines of the assembly are shaped to deform in a predetermined manner and/or at predetermined locations with greater predictability in response to an axial force acting on the assembly from either its distal end or its proximal end. Advantageously, the spines readily flex in the portions of greater flexibility much like "shock absorbers," enabling the assembly to compress axially and absorb and dampening forces that may otherwise damage tissue, yet retain sufficient shape and rigidity for ensuring contact with tissue wall and electrode space. In some embodiments, a portion of greater flexibility in the spine has a smaller cross-section, for example, a lesser thickness and/or a lesser width relative to the remaining portion(s) of the spine with lesser flexibility by comparison. In some embodiments, the lesser thickness and/or lesser width are provided by one or more notches that may be oriented laterally on the spine, or on an inner or outer surface of the spine. The notch may have a generally smooth contour or a stepped contour.

In accordance with a feature of the present invention, one or more spines of the basket-shaped electrode assembly may have one or more regions of greater flexibility that enable the assembly to compress longitudinally in response to an axial force. In some embodiment, at least one spine has an equatorial portion with greater flexibility, and distal and proximal portions of the spine with lesser flexibility by comparison, where the equatorial portion flexes more readily than the distal and proximal portions, and the spine flexes into a V shape with a greater or acute bend in the equatorial portion. In some embodiments, a spine has first and second portions of greater flexibility separated by a mid-portion of lesser flexibility, where the first and second portions flex more readily than the mid-portion and/or the distal and proximal portions, and the spine flexes into a U shape with two greater or acute bends between the mid-portion.

BRIEF DESCRIPTION OF THE DRAWINGS

These and other features and advantages of the present invention will be better understood by reference to the following detailed description when considered in conjunction with the accompanying drawings wherein:

FIG. 2 is a detailed view of the basket-shaped electrode assembly of FIG. 1, in a collapsed configuration.

FIG. 3A is a side cross-sectional view of the catheter of the present invention, including a junction between a catheter body and a deflection section, along a diameter.

FIG. 5A is a top view of a cabling for use with the present invention, according to one embodiment, with part(s) broken away.

FIG. 5B is an end cross-sectional view of the cabling of FIG. 5A.

FIG. 5C is a side view of the cabling of FIG. 5A, with part(s) broken away.

DETAILED DESCRIPTION OF THE INVENTION

The present invention is directed to a catheter 10 having a basket-shaped assembly 18 with at least a region of greater flexibility and at least a region or portion of lesser flexibility by comparison relative to the region of greater flexibility which enable the basket-shaped assembly 18 to readily flex in a predetermined manner and absorb excessive forces that may otherwise result in injury or damage to tissue, for example, when the assembly 18 unexpectedly encounters anatomy or when the assembly 18 is pressed excessively against tissue. The catheter of the present invention provides this flexibility without significant compromise in the shape, structure and sufficient rigidity of the assembly in providing dependable tissue contact and electrode spacing.

Figure 1:
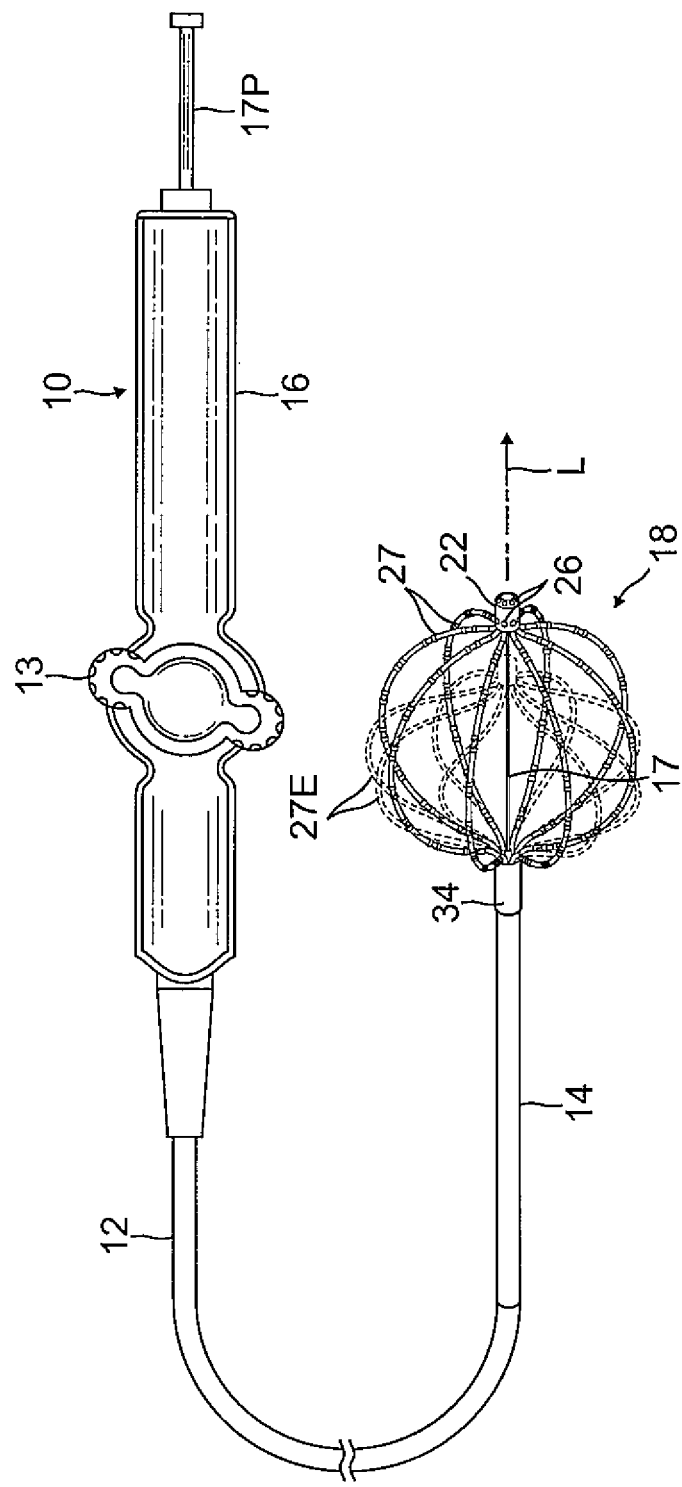
FIG. 1 is a top plan view of a catheter of the present invention, according to one embodiment, with a basket-shaped electrode assembly in an expanded, deployed configuration.

As shown in FIG. 1, the catheter 10 comprises an elongated catheter body 12 having proximal and distal ends, a control handle 16 at the proximal end of the catheter body, an intermediate deflection section 14 distal of the catheter body 12, and the basket-shaped electrode assembly 18 at the distal end of the deflection section 14. The basket-shaped electrode assembly (or "assembly") 18 has a plurality of spines 27 whose proximal ends and distal ends surround an elongated expander 17 that is afforded longitudinal movement relative to the catheter for adjusting the shape of the assembly between an expanded configuration (FIG. 1) and a collapsed configuration (FIG. 2). In the illustrated embodiment of FIG. 1, the basket-shaped assembly 18 has at least one region of greater or hyper flexibility, for example, an equatorial region 27E, that enables the assembly to deform in a predetermined and predictable manner, including forming a greater or acute flexion at the equatorial region 27E and compressing or shortening in the longitudinal direction to absorb excessive force in the axial direction along longitudinal axis L of the catheter.

With reference to FIG. 3A, the catheter body 12 comprises an elongated tubular construction having a single, axial or central lumen 15, but can optionally have multiple lumens if desired. The catheter body 12 is flexible, i.e., bendable, but substantially non-compressible along its length. The catheter body 12 can be of any suitable construction and made of any suitable material. One construction comprises an outer wall 20 made of polyurethane or PEBAX® (polyether block amide). The outer wall 20 comprises an imbedded braided mesh of stainless steel or the like to increase torsional stiffness of the catheter body 12 so that, when the control handle 16 is rotated, the distal end of the catheter body will rotate in a corresponding manner.

The outer diameter of the catheter body 12 is not critical, but may be no more than about 8 french, more preferably 7 french. Likewise the thickness of the outer wall is not critical, but is preferably thin enough so that the central lumen 15 can accommodate a puller wire, lead wires, sensor cable and any other wires, cables or tubes. If desired, the inner surface of the outer wall is lined with a stiffening tube 21 to provide improved torsional stability. An example of a catheter body construction suitable for use in connection with the present invention is described and depicted in U.S. Pat. No. 6,064,905, the entire disclosure of which is incorporated herein by reference.

Figure 3B:
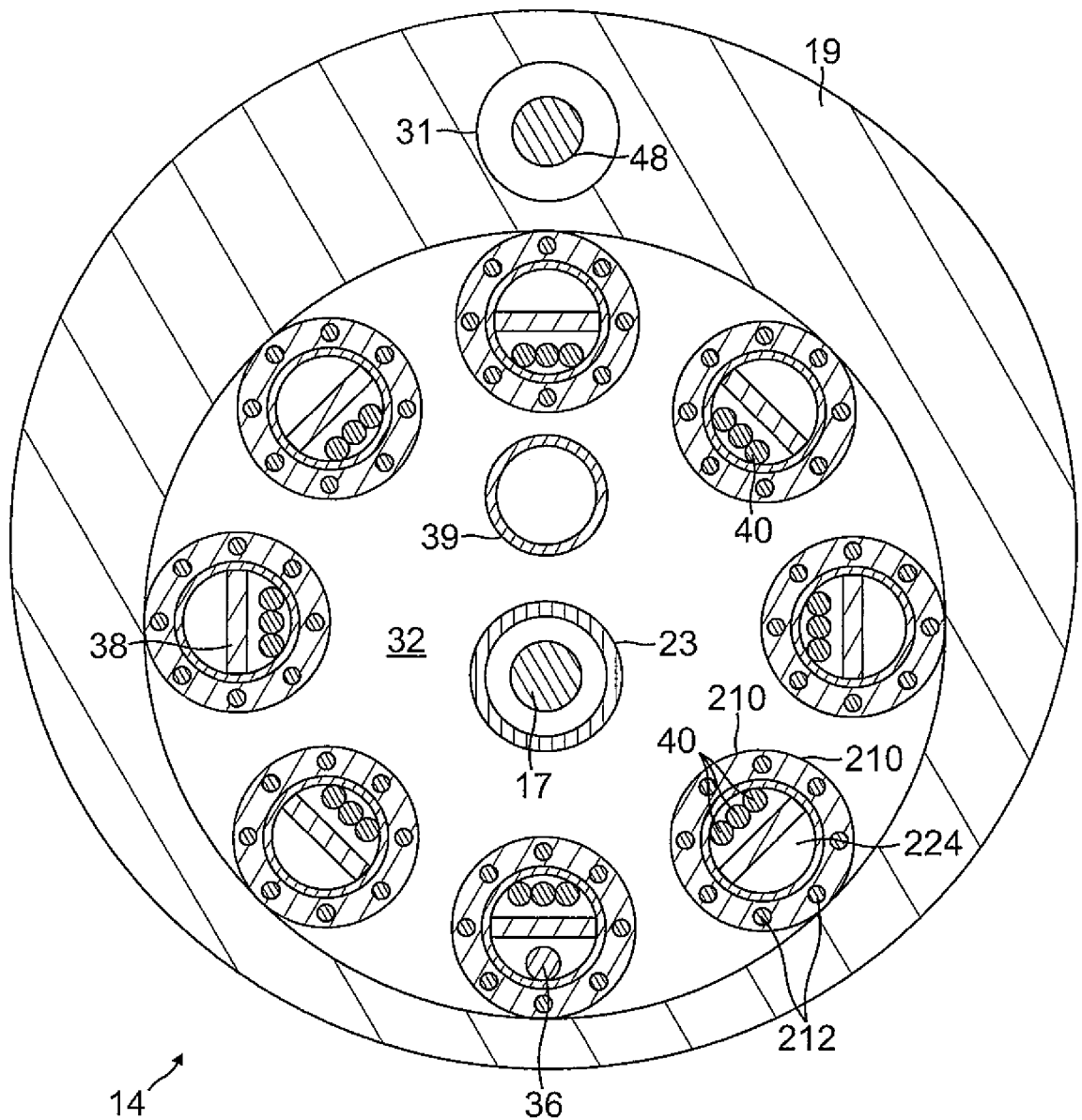
FIG. 3B is an end cross-sectional view of the deflection section of FIG. 3A, taken along line B-B.

Distal of the catheter body 12 is the intermediate deflection section 14 which comprises a multi-lumened tubing 19, with, for example, at least two off axis lumens 31 and 32, as shown in FIGS. 3A and 3B. The multi-lumened tubing 19 is made of a suitable non-toxic material that is preferably more flexible than the catheter body 12. In one embodiment, the material for the tubing 19 is braided polyurethane or thermoplastic elastomer (TPE), for example, polyether block amide (PEBAX®), with an imbedded mesh of braided high-strength steel, stainless steel or the like. The outer diameter of the deflection section 14 is no greater than that of the catheter body 12. In one embodiment, the outer diameter is no greater than about 8 french, more preferably about 7 french. Larger or smaller embodiments are possible, as determined by the number of spines in the basket, if applicable. The size of the lumens is not critical, so long as the lumens can accommodate the components extending therethrough.

A means for attaching the catheter body 12 to the deflection section 14 is illustrated in FIG. 3A. The proximal end of the deflection section 14 comprises an outer circumferential notch 24 that receives the inner surface of the outer wall 20 of the catheter body 12. The deflection section 14 and catheter body 12 are attached by adhesive (e.g. polyurethane glue) or the like. Before the deflection section 14 and catheter body 12 are attached, however, the stiffening tube 21 is inserted into the catheter body 12. The distal end of the stiffening tube 21 is fixedly attached near the distal end of the catheter body 12 by forming a glue joint (not shown) with polyurethane glue or the like. Preferably, a small distance, e.g., about 3 mm, is provided between the distal end of the catheter body 12 and the distal end of the stiffening tube 21 to permit room for the catheter body 12 to receive the notch 24 of the deflection section 14. A force is applied to the proximal end of the stiffening tube 21, and, while the stiffening tube 21 is under compression, a first glue joint (not shown) is made between the stiffening tube 21 and the outer wall 20 by a fast drying glue, e.g. Super Glue®. Thereafter, a second glue joint (not shown) is formed between the proximal ends of the stiffening tube 21 and outer wall 20 using a slower drying but stronger glue, e.g. polyurethane.

Figure 4A:
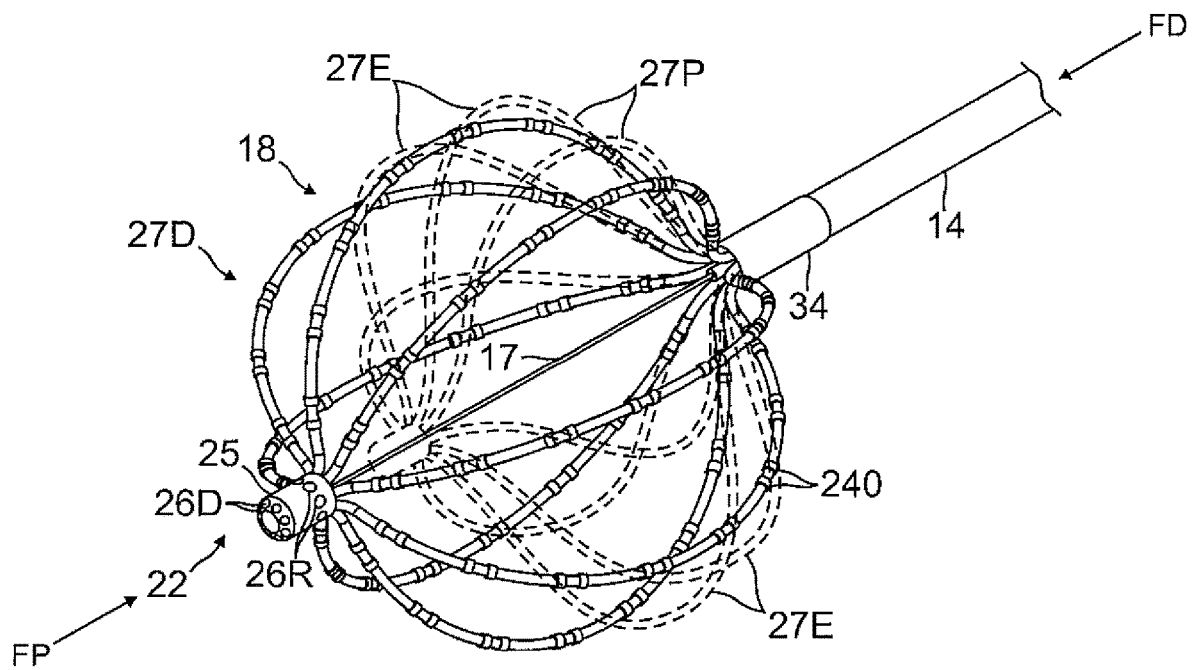
FIG. 4A is a detailed view of the basket-shaped electrode assembly of FIG. 1, in an expanded, deployed configuration.
Figure 4B:
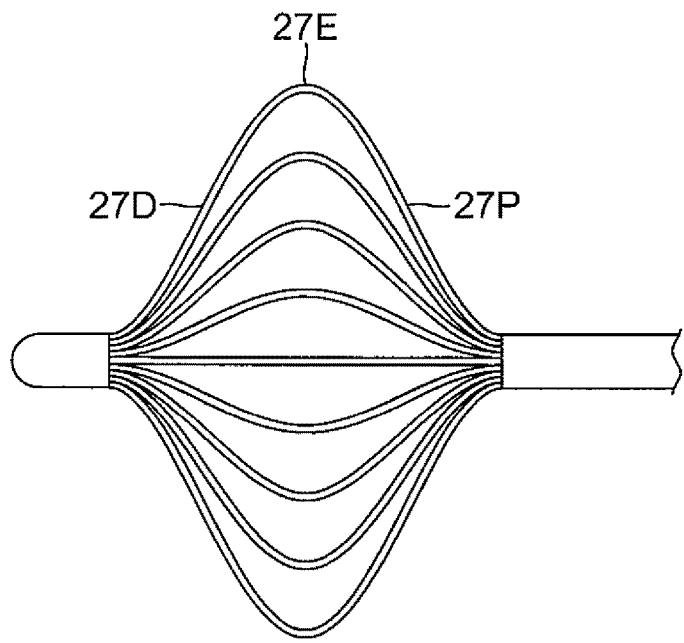
FIG. 4B is a side elevational view of the assembly of FIG. 4A, in a hyper-flexed configuration.
Figure 4C:
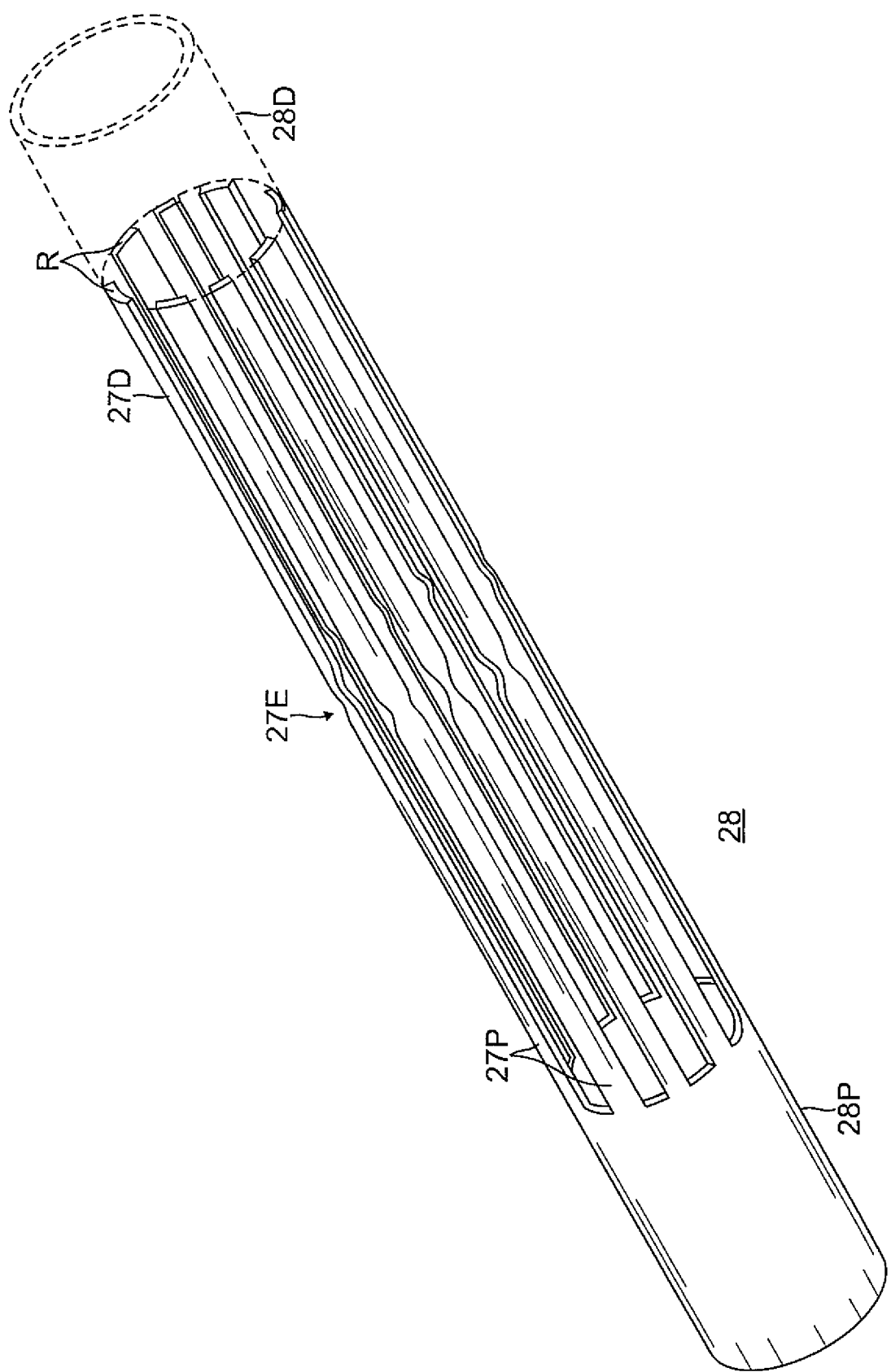
FIG. 4C is a perspective view of a cylindrical body forming spines of the basket-shaped electrode assembly, in accordance with one embodiment.

The basket-shaped electrode assembly 18 is mounted to the distal end of the catheter body 12. As shown in FIGS. 1 and 4A, the basket-shaped electrode assembly 18 comprises a plurality of electrode-carrying spines 27 or arms (e.g., between about five to ten, and preferably about eight) mounted, generally evenly-spaced in about 360 radial degrees around the expander 17 so that the expander forms the center longitudinal axis L of the electrode assembly. Each of the spines 27 is attached, directly or indirectly, at its distal end to the distal end of the expander 17. In some embodiments, the spines 27 are formed from a cylindrical body 28, as shown in FIG. 4C, which has been cut, for example, by laser, to provide the plurality of spines 27 separated by gaps, each having a free distal end. In the illustrated embodiment, a proximal end of the cylindrical body 28 remains intact to form a proximal stem 28P; however, it is understood that a distal stem 28D may also remain intact, as desired or needed. Accordingly, in these embodiments, each spine may have a rectangular cross-section R. As actuated by longitudinal movement of the expander 17 relative to the catheter, the assembly 18 is adapted to assume an elongated and collapsed configuration with the expander 17 extended distally (FIG. 2) and a deployed and radially expanded configuration with the expander drawn proximally (FIG. 1). The expander 17 comprises a material sufficiently rigid to achieve this function. In an embodiment, the expander 17 is a wire or tensile member, and a guide tube 23 is provided to surround, protect and guide the expander 17 through the control handle 16, the catheter body 12 and the deflection section 14. The guide tube 23 is made of any suitable material, including polyimide.

In one embodiment, each spine 27 of the assembly 18 comprises a cabling 210 with build-in or embedded lead wires 212, as shown in FIGS. 5A, 5B and 5C. The cabling has a core 218, and a plurality of generally similar wires 212 covered by an insulating layer 216 that enables each wire to be formed and to function as a conductor 214. The core 218 provides a lumen 224 in which can pass other components such as additional lead wire(s), cables, tubing and/or a support structure to shape the cabling as desired.

In the following description, generally similar components associated with cabling 210 are referred to generically by their identifying component numeral, and are differentiated from each other, as necessary, by appending a letter A, B, . . . to the numeral. Thus, wire 212C is formed as conductor 214C covered by insulating layer 216C. While embodiments of the cabling may be implemented with substantially any plurality of wires 212 in the cabling, for clarity and simplicity in the following description cabling 210 is assumed to comprise N wires 212A, 212B, 212C, . . . 212N, where N equals at least the number of ring electrodes on each respective spine of the assembly 18. For purposes of illustration, insulating layers 216 of wires 212 have been drawn as having approximately the same dimensions as conductors 214. In practice, the insulating layer is typically approximately one-tenth the diameter of the wire.

The wires 212 are formed over an internal core 218, which is typically shaped as a cylindrical tube, and core 218 is also referred to herein as tube 218. The core material is typically selected to be a thermoplastic elastomer such as a polyether block amid (PEBA) or PEBAX® Wires 212 are formed on an outer surface 220 of the core 218 by coiling the wires around the tube 218. In coiling wires 212 on the surface 220, the wires are arranged so that they contact each other in a "close-packed" configuration. Thus, in the case that core 218 is cylindrical, each wire 212 on the outer surface is in the form of a helical coil. In the case of the tube 218 being cylindrical, the close packed arrangement of the helical coils of wires 212 means that the wires are configured in a multi-start thread configuration. Thus, in the case of the N wires 212 assumed herein, wires 212 are arranged in an N-start thread configuration around cylindrical tube 218.

In contrast to a braid, all helical coils of wires 212 herein have the same handedness (direction of coiling). Moreover, wires in braids surrounding a cylinder are interleaved, so are not in the form of helices. Because of the non-helical nature of the wires in braids, even braid wires with the same handedness do not have a threaded form, let alone a multi-start thread configuration. Furthermore, because of the lack of interleaving in arrangements of wires in embodiments of the cabling, the overall diameter of the cabling produced is less than that of cabling using a braid, and the reduced diameter is particularly beneficial when the cabling is used for a catheter.

Once wires 212 have been formed in the multi-start thread configuration described above, the wires are covered with a protective sheath 222. The protective sheath material is typically selected to be a thermoplastic elastomer such as PEBA, for example, 55D PEBAX without additives so that it is transparent. In that regard, insulating layer of at least one of wires 212 is colored differently from the colors of the remaining wires as an aid in identifying and distinguishing the different wires.

The process of coiling wires 212 around the core 218, and then covering the wires by the sheath 222 essentially embeds the wires within a wall of cabling 210, the wall comprising the core and the sheath. Embedding the wires within a wall means that the wires are not subject to mechanical damage when the cabling is used to form a catheter. Mechanical damage is prevalent for small wires, such as 48AWG wires, if the wires are left loose during assembly of a catheter.

In use as a catheter, an approximately cylindrical volume or lumen 224 enclosed by the core 218, that is afforded by embedding smaller wires (such as the 48 AWG wires) in the wall, allows at least a portion of the lumen 224 to be used for other components. It is understood that the plurality of wires 212 shown in the drawings is representative only and that a suitable cabling provides at least a plurality of wires equal to or greater than the plurality of ring electrodes mounted on each cabling or spine of the assembly. Cabling suitable for use with the present invention is described in U.S. Publication No. 2014/0309512 and U.S. Publication No. 2014/0305699, the entire disclosures of which are incorporated herein by reference. Each cabling 210 (with embedded lead wires 212) extends from the control handle 16, through the lumen 15 of the catheter body 12, and the larger lumen 32 of the tubing 19 of the deflection section 14, as shown in FIG. 3A.

Figure 6A:
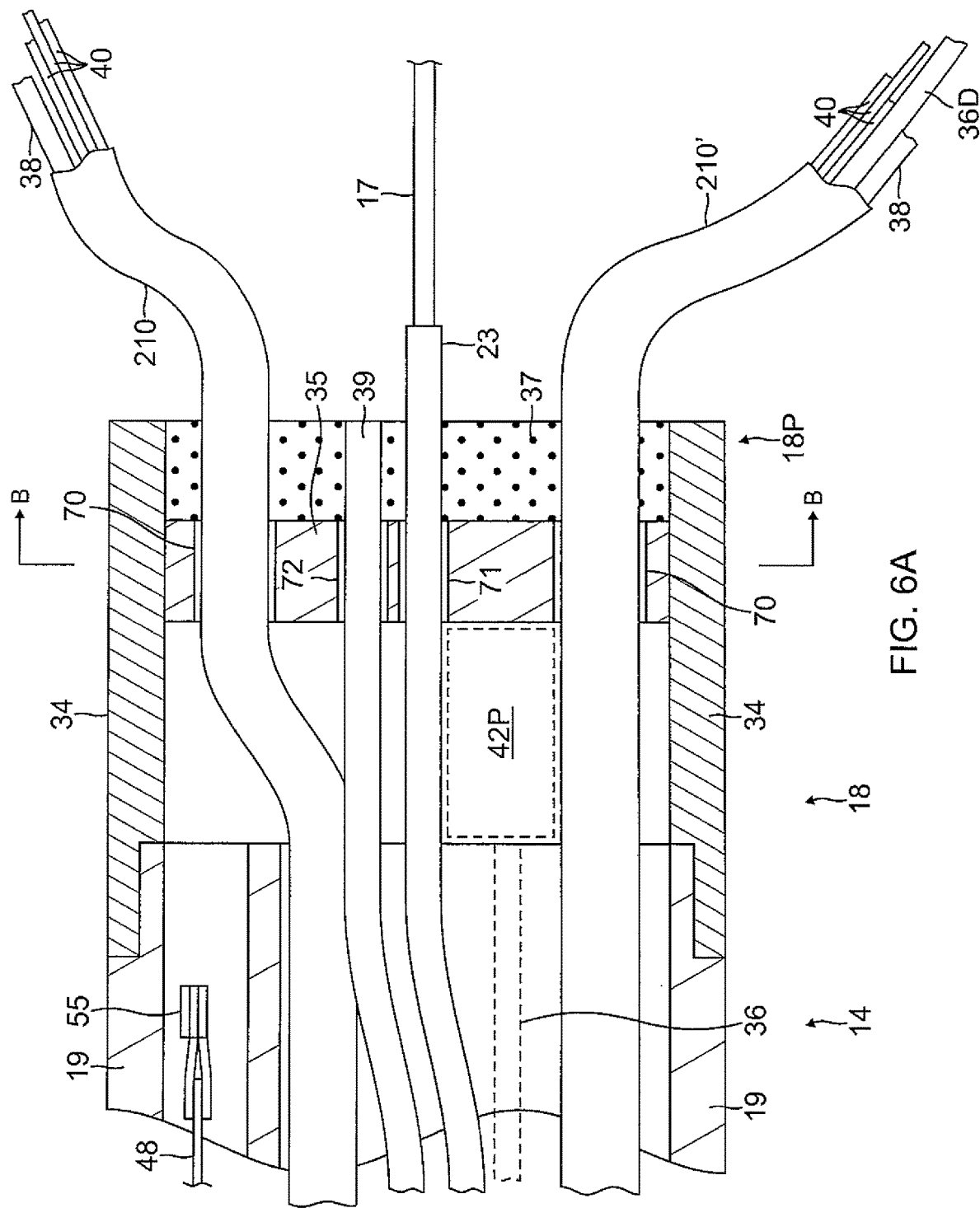
FIG. 6A is a side cross-sectional view of a proximal junction of the basket-shaped electrode assembly, according to one embodiment.
Figure 6B:
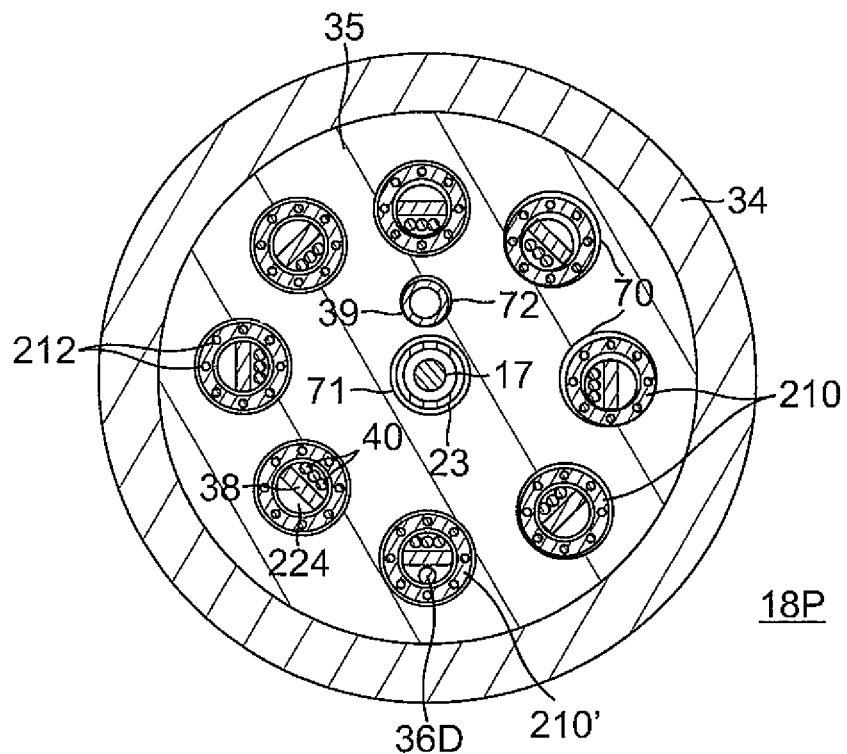
FIG. 6B is an end cross-section view of the proximal junction of FIG. 6A, taken along line B-B.

With reference to FIGS. 6A and 6B, at the proximal end of the assembly 18, the cabling 210 (serving as the spines 27 of the assembly 18, and used interchangeably herein) extend through a proximal junction 18P that includes an outer tubing 34 that extends a short distance from the distal end of the tubing 19 of the deflection section 14. The outer tubing 34 may be made of any suitable material, for example, PEEK (polyetheretherketone).

In the lumen of the outer tubing 34, a proximal alignment disc 35 formed with a plurality of through-holes is provided to receive and position the cabling 210 and the guide tube 23 of the expander 17 in the outer tubing 34. The proximal disc 35 is made of any suitable material, including metal or plastic. In the embodiment of FIGS. 6A and 6B, the proximal disc 35 has an on-axis through-hole 71 for the guide tube 23, and a plurality of off-axis through-holes 70 around a peripheral region of the disc, with each through-hole guiding a respective cabling 210 (only two of which are shown in FIG. 6A for clarity). For example, with eight cabling 210, the through-holes 70 are situated at about 45 radial degrees around the peripheral region. Where irrigation is desired, the disc 35 includes another off-axis through-hole 72 which receives a distal end of an irrigation tubing 39 from which fluid passing through the tubing 39 exits the catheter. Distal of the disc 35, the lumen of the outer tubing 34 is filled and sealed with a suitable glue 37, for example, epoxy.

The cabling 210 and the expander 17 extend distally from the proximal junction 18P to form the assembly 18. Each cabling has a predetermined shape flexibly set by a shape memory member 38 that extends through the lumen 224 in the core 218. As shown in FIG. 3B, selected or all of the lumens 224 of the cores 218 also carry additional lead wires 40 for the array of microelectrodes 26 on the distal tip 22. Selected lumens 224 may also carry cable(s) 36 for electromagnetic location sensor(s) carried in the distal tip 22.

In forming the basket shape, the shape memory members 38 in the cabling 210 diverge from the proximal junction 18P and bow outwardly from the expander 17, and converge at their distal ends at the distal tip 22, as shown in FIG. 4A. The shape memory member 38, e.g., a Nitinol shape member or wire, is configured to flexibly provide the shape of the basket-assembly, as known in the art. In one embodiment, the shape memory member 38 of each cabling 210 has a proximal end located near the proximal end of the deflection section 14, and a distal end located in the distal tip 22, although it is understood that the proximal end may be located anywhere proximally of the proximal end of the deflection section 14 along the length of the cabling 210, as desired or appropriate.

As understood by one skilled in the art, the number of spines 27 or cabling 210 of the assembly 18 can vary as desired depending on the particular application, so that the assembly 18 has at least two spines, preferably at least three spines, and as many as eight or more spines. As used herein, the term "basket-shaped" in describing the electrode assembly 18 is not limited to the depicted configuration, but can include other designs, such as spherical or egg-shaped designs, that include a plurality of expandable arms connected, directly or indirectly, at their proximal and distal ends.

Figure 8A:
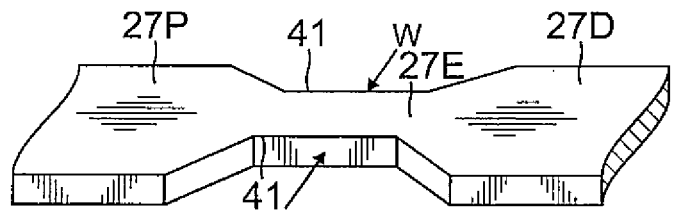
FIG. 8A is a perspective view of a spine with stepped lateral notched regions, in accordance with an embodiment of the present invention.
Figure 8B:
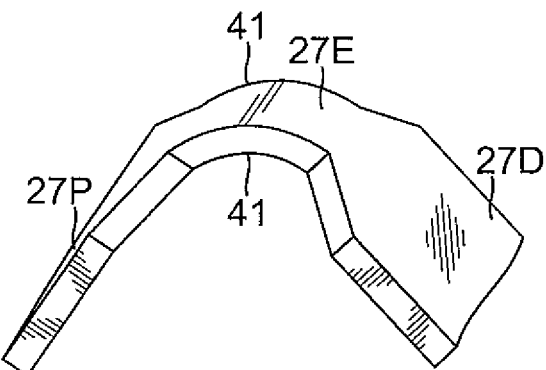
FIG. 8B is a perspective view of the spine of FIG. 8A in a flexed configuration.
Figure 9A:
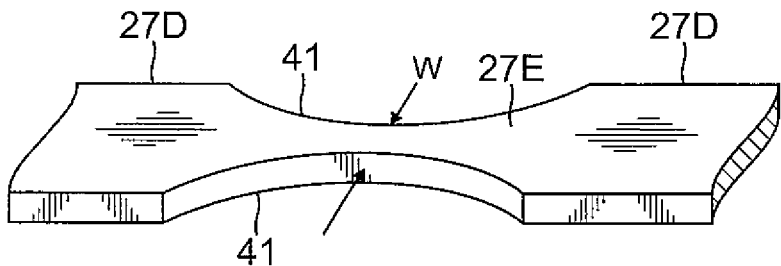
FIG. 9A is a perspective view of a spine with smooth lateral notched regions, in accordance with an embodiment of the present invention.
Figure 9B:
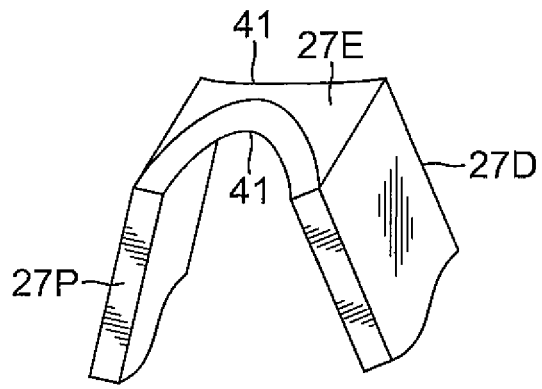
FIG. 9B is a perspective view of the spine of FIG. 9A in a hyper-flexed configuration.
Figure 10A:
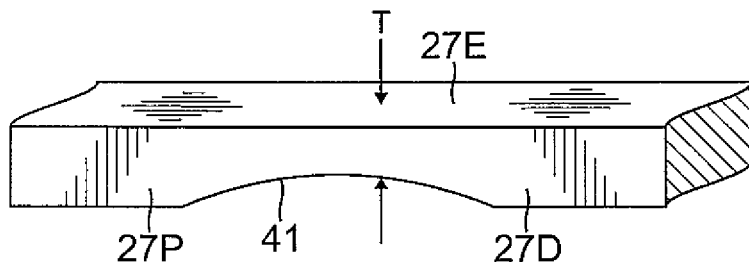
FIG. 10A is a perspective view of a spine with a smooth inner notched region, in accordance with an embodiment of the present invention.
Figure 10B:
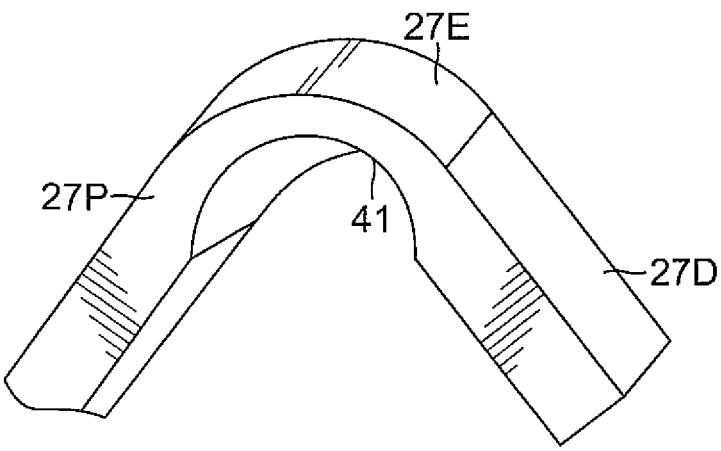
FIG. 10B is a perspective view of the spine of FIG. 10A in a hyper-flexed configuration.
Figure 11A:
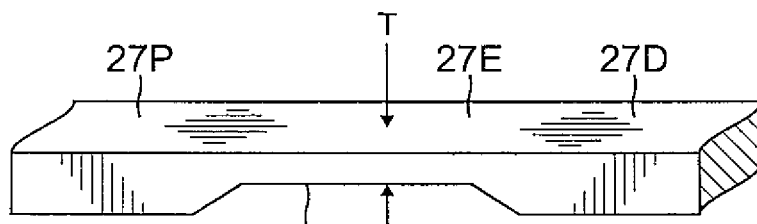
FIG. 11A is a perspective view of a spine with a stepped inner notched region, in accordance with an embodiment of the present invention.
Figure 11B:
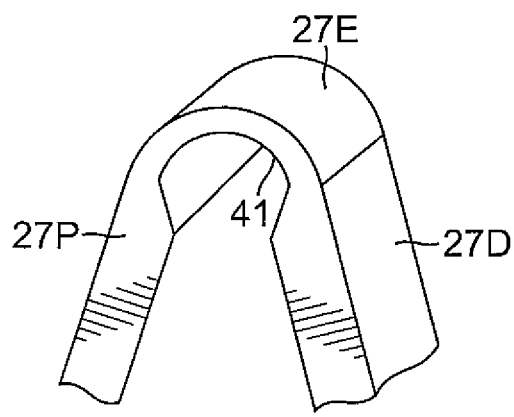
FIG. 11B is a perspective view of the spine of FIG. 11A in a hyper-flexed configuration.
Figure 12A:
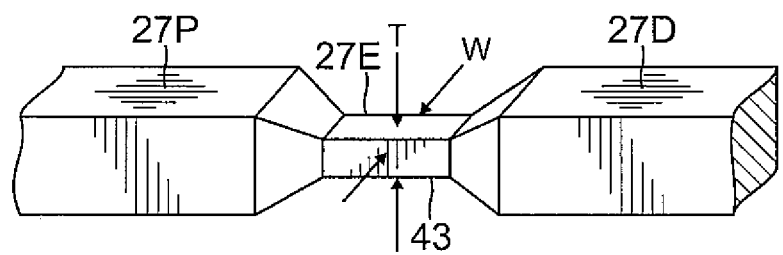
FIG. 12A is a perspective view of a spine with a stepped waist region, in accordance with an embodiment of the present invention.
Figure 12B:
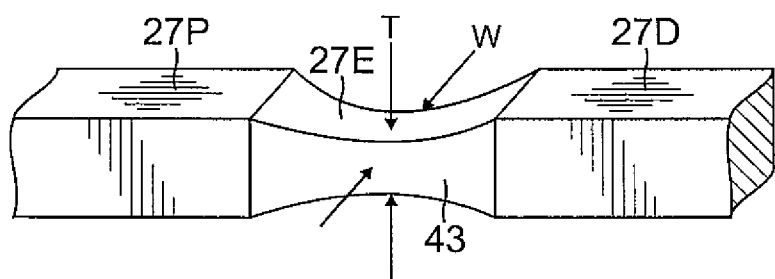
FIG. 12B is a perspective view of a spine with a smooth waist region, in accordance with an embodiment of the present invention.

In accordance with a feature of the present invention, the assembly 18 has a structure that facilitates contact with surrounding tissue wall while minimizing risk of injury to the tissue wall. In that regard, the assembly has a greater stiffness near its proximal ends and a greater flexibility therebetween. In some embodiments, one or more spines 27 have at least one region with greater flexibility relative to their proximal and distal regions. As shown in the embodiment of FIG. 4C, spine 27 has an equatorial region 27E with a different configuration (including a different and/or smaller cross section) that enables greater flexibility compared to distal region 27D and proximal region 27P. For example, the different configuration includes one or more indented regions or lateral notches 41 defining a lesser width dimension W (FIGS. 8A and 9A), one or more inner and outer notches 41 defining a lesser thickness dimension T (FIGS. 10A and 11B), or a waist region 43 defined by both a lesser width dimension and a lesser thickness dimension (FIGS. 12A and 12B). The notches 41 providing the transition between the different dimensions along the length of the spines may have a continuous or smooth contour (FIGS. 8A and 11A), or it may have a discontinuous or stepped contour (FIGS. 9A and 10A).

The region of greater flexibility enables the spine to readily deform so as to absorb any additional or excessive force when the assembly 18, including its distal end or the distal tip electrode 22, contacts tissue either intentionally (such as when an axial force is applied by an EP professional to purposefully expand the assembly) or unintentionally (such as when the distal tip electrode 22 encounters anatomy unexpectedly. As illustrated in FIGS. 8B, 9B, 10B, and 11B, the region 27E of the spine readily flexes and bows such that the assembly 18 can shorten and collapse longitudinally into a hyper-expanded configuration, as shown in broken lines in FIG. 4A, to minimize the risk of the distal tip electrode 22 causing damage or injury, such as perforation of the tissue wall, without compromising the structure and stiffness of the proximal and distal regions 27P and 27D of the spines. In the illustrated embodiment of FIG. 4A, the equatorial region 27E of greater or hyper flexibility readily deforms and bends to form a greater or acute bend so that the assembly 18 is compressed longitudinally to absorb a force acting on the assembly from either its distal end or its proximal end. When compressed, the spines 27 can deform into more of a V-shape configuration with the assembly 18 able to deform and flatten into a shape resembling a pattypan or scallop squash, as better shown in FIG. 4B (without electrodes for clarity), with a visibly shortened longitudinal length and a visibly pronounced ridge-like equatorial region 27E, with the distal and proximal portions 27D and 27P experiencing minimal deformation. Advantageously, the regions of greater flexibility in the spines allow the spine to readily elastically change between a first configuration with a generally uniform flexed curvature along its length to a second configuration having a generally uniform curvature at the distal and proximal regions separated by a hyper or more acute curvature in an equatorial region.

Each spine 27 or cabling 210 carries a plurality of ring electrodes 240, which may be configured as monopolar or bipolar, as known in the art. FIGS. 5A and 5B are schematic diagrams illustrating attachment of a ring electrode 240 to cabling 210, according to an embodiment. FIG. 5A is a schematic top view of the cabling and FIG. 5B is a schematic side view of the cabling; in both views portions of sheath 222 have been cut away to expose wires 212 of the cabling 210, as well as to illustrate the attachment of a ring electrode 240 to the cabling 210. FIG. 5A illustrates cabling 210 before attachment of ring electrode 240, and FIG. 5B illustrates the cabling after the ring electrode has been attached. Ring electrode has dimensions enabling it to be slid over sheath 222.

Initially a location for attaching a ring electrode 240 is selected by visually finding a colored wire, such as wire 212E. The visual determination is possible since sheath 222 is transparent. Once the location has been selected, a section of sheath 222 above the wire and a corresponding section of insulating layer 216E are removed to provide a passage 242 to conductor 214E. In a disclosed embodiment, conductive cement 244 is fed into the passage, ring electrode 240 is slid to contact the cement, and the electrode is then crimped in place. Alternatively, the ring electrode 240 may be attached to a specific wire by pulling the wire through sheath 222, and resistance welding or soldering the ring electrode to the wire.

Figure 7A:
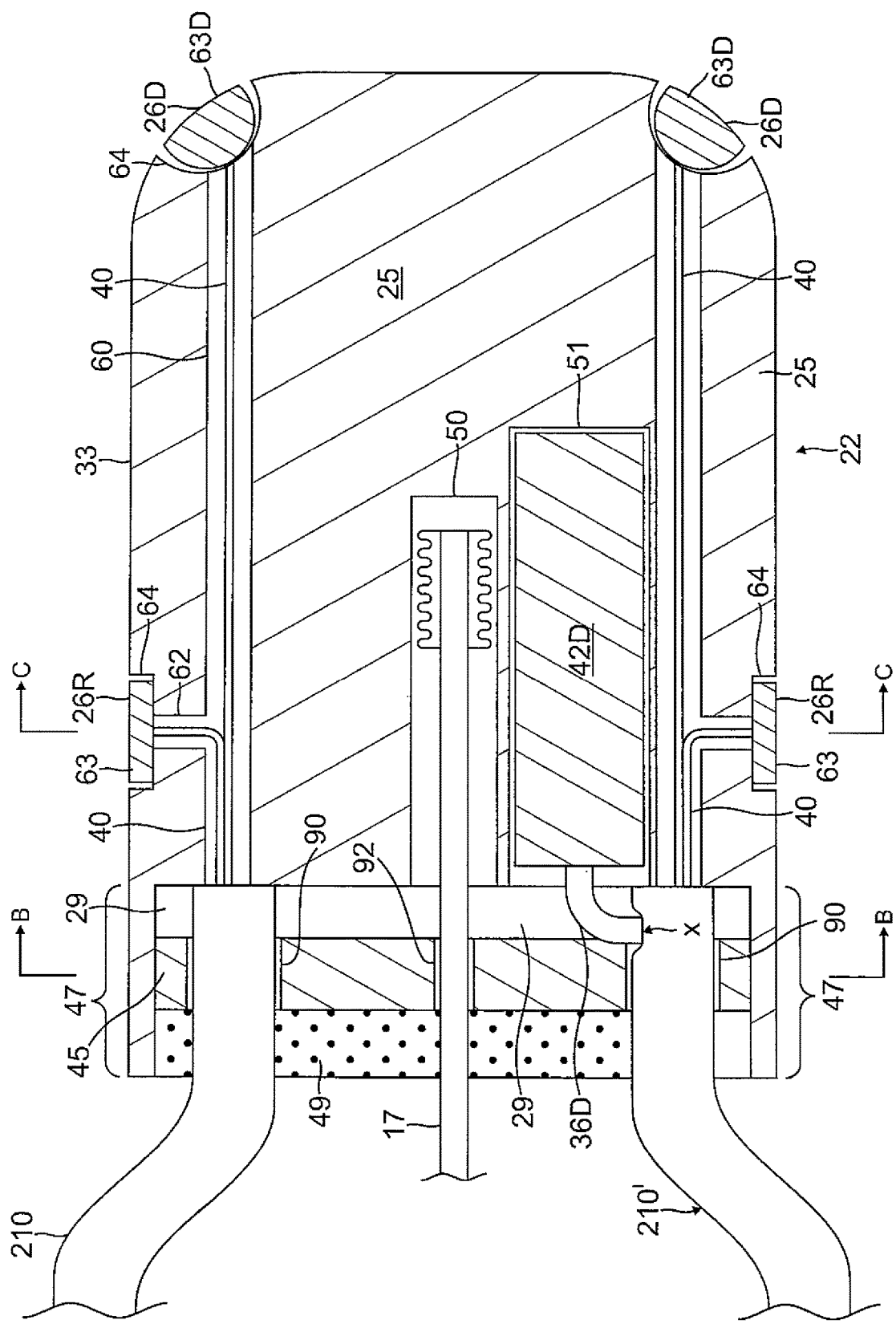
FIG. 7A is a side cross-sectional view of a distal tip, in accordance with one embodiment.
Figure 7B:
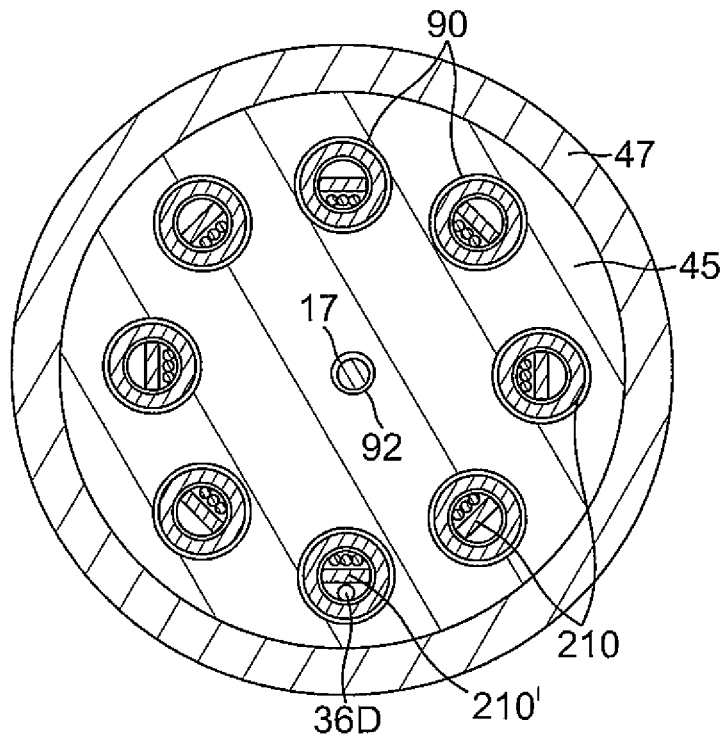
FIG. 7B is an end cross-sectional view of the distal tip of FIG. 7A, taken along line B-B.

With reference to FIGS. 7A and 7B, at the distal end of the assembly 18, the distal ends of the cabling 210 converge around the distal end of the expander 17 in the distal tip 22. The distal tip 22 has a generally solid, elongated, nonmetallic, electrically-insulating substrate body 25 with a generally cylindrical shape (with a two-dimensional curvature in the X/Y direction and a linear length in the Z direction), and a domed distal end (with a three-dimensional curvature in the X/Y/Z direction). The body has a trepanned proximal face 47 forming a cored-out proximal region 29 in which the distal ends of the cabling 210 and the expander 17 are received, anchored and sealed by glue 49, for example, epoxy. A first, on-axis blind hole 50 extends distally from the cored-out proximal region to receive a crimped distal tip of the expander 17. A second, off axis blind hole 52 extends distally from the cored-out proximal region 29 to receive at least a portion of the electromagnetic location sensor 42.

The distal ends of the cabling 210 in the cored-out proximal region 29 are positioned by a distal alignment disc 45. The disc 45 has a plurality of through-holes to receive the cabling 210 and the expander 17 in the outer tubing 34. The disc 45 is made of any suitable material, including metal or plastic. In the embodiment of FIGS. 7A and 7B, the distal disc 45 has an on-axis through-hole 92 for the expander 17, and a plurality of off-axis through-holes 90 around a peripheral region of the disc, with each through-hole guiding the distal end of a respective cabling 210 (only two of which are shown in FIG. 7A for clarity). For example, with eight cabling 210, the through-holes 90 are situated at about 45 radial degrees around the peripheral region. Proximal of the disc 45, the cored-out proximal region 29 is filled and sealed with a suitable glue 49, for example, epoxy.

Also formed in the body 25 of the distal tip 22 are axial passages 60 and radial passages 62, as shown in FIG. 7A, providing communication between the cored-out proximal region 29 and indentations 64 formed on outer surface 33 of the body 25 where the microelectrodes 26 are located. With respective pairs of the cabling 210 and axial passages 60 axially aligned with each other in the tip 22, the additional lead wires 40 that pass through the lumen 224 of the core 218 of the cabling 210 extend through the axial and radial passages 60 and 62 for connection to the respective microelectrodes and/or temperature sensing in the distal tip 22. Radial microelectrodes 26R are located on radial outer surface of the body 25. Distal microelectrodes 26D are located on distal outer surface of the body 25. It is understood that the plurality of wires 40 shown in the drawings is representative only and that the plurality of wires is equal to or greater than the plurality of microelectrodes carried on the distal tip 22. Also passing through the lumen 224 of the core 218 of one predetermined cabling 210' is the cable 36D for the distal EM location sensor 42D. A portion of the wall of the cabling 210' is removed at X so as to accommodate the cable 36D extending from a distal EM location sensor 42D.

Figure 7C:
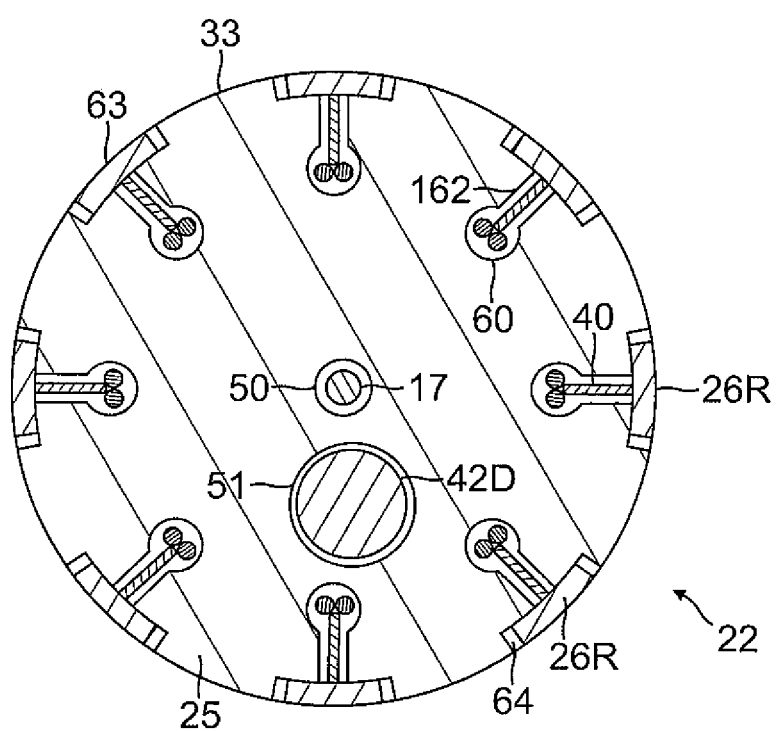
FIG. 7C is an end cross-sectional view of the distal tip of FIG. 7A, taken along line C-C.

In accordance with a feature of the present invention, the indentations 64 are shaped and sized in correspondence with the shape and size of the microelectrode 26 which has a body that is fully received in a respective indentation 64 such that only an outer or outer-facing surface 63 of the microelectrode is exposed and generally even and flush with the outer surface 33 of the body 25 of the distal tip 22, as shown in FIGS. 7A and 7C. The indentations 64 allow the microelectrodes 26 to be recessed in the body 25 to provide a smooth and atraumatic profile which minimizes the risk of the microelectrodes snagging, scratching or otherwise damaging tissue in contact with the distal tip 22. Each indentation minimizes, if not prevents, contact between tissue and a microelectrode except by the outer surface 63 of the microelectrode. The indentation limits tissue contact by any side surface or inner surface of a microelectrode by surrounding the microelectrode except for the outer surface.

Moreover, the outer surface 63 of the microelectrode 26 has the same contour as the surrounding outer surface 33 of the substrate body 25. For example, the distal microelectrodes 26D have three-dimensionally curved outer surfaces 63D that conform with the three-dimensionally curved outer surface 33 of the substrate body 25 at its distal end, and the radial microelectrodes 26R have two-dimensionally curved outer surfaces 63R that conform with the two-dimensionally curved outer surfaces 33 of the substrate body 25. With a generally smooth profile, the tip 22 can be pivoted about its distal end in a circular motion where its longitudinal axis traces a cone C to improve electrode contact with minimum risk of damage to tissue, especially in a cavernous region, such as an atrium.

Each microelectrode 26 has a surface area ranging between about 0.05 mm$^2$ and 0.5 mm$^2$, and preferably 0.15 mm$^2$. Thus, the distal tip 22 comprises a plurality of tiny, closely spaced electrodes that may be formed from any suitable material, including medical-grade metal, for example, palladium, platinum, gold, stainless steel and the like, and combinations thereof. With a large number of microelectrodes 26, the tip 22 advantageously provides focal diagnostic capabilities with precisely known microelectrode locations by means of their fixed location relative to the tip body 25, whereas the assembly 18 with its large number of ring electrodes 240 on the spines 27 allows the physician to more quickly cover a large area of internal geometry of a cavernous region, such as the heart.

Each of the ring electrodes 240 on the spines 27 and each of the microelectrodes 26 is electrically connected via the lead wires 212 and 40, respectively, to an appropriate mapping system and/or source of ablation energy remote from the catheter by means of a multi-pin connector (not shown) at the proximal end of the control handle 16. The cabling 210 with embedded electrode lead wires 212 in its wall and additional lead wires 40 and EM sensor cable 36 in its lumen 224 pass from the control handle 16 and through the central lumen 15 of the catheter body 12 and the lumen 32 of the deflection section 14 and extends through the assembly 18 as the spines where lead wires 212 are connected to the ring electrodes, the lead wires 40 are connected to the microelectrodes 26 on the distal tip 22 and the cable 36 to the EM sensor in the distal tip 22. By combining the assembly 18 with a microelectrode distal tip 22, the catheter is adapted for both large area mapping and acute focal mapping.

The expander 17 has a suitable length that extends the entire length of the catheter. The expander includes a proximal end 17P (FIG. 1) that is exposed proximally of the control handle 16, a main portion that extends through the control handle 16, the central lumen 15 of the catheter body 12, and the lumen 32 of the deflection section 14, and an exposed distal portion extending through the assembly 18 and into the distal tip 22. The guide tube 23 extends through the control handle 16, the central lumen 15 of the catheter body, and the lumen 32 of the deflection section 14 and has distal end that extends a short distance distal of the distal end of the outer tubing 34 of the proximal junction 18P of the assembly 18. A user manipulates the proximal end 17P by advancing or withdrawing the expander 17 longitudinally relative to the control handle 16 and the catheter so that it can move the distal ends of the spines 27 proximally or distally relative to the catheter to radially expand and contract, respectively, the assembly 18.

As shown in FIGS. 3A and 3B, a puller wire 48 for uni-directional deflection of the deflection section 14 extends from the control handle 16 where its proximal end is anchored and responsive to a deflection knob 13 on the control handle 16, and through the central lumen 15 of the catheter body 12 and the lumen 31 of the deflection section 14. As shown in FIG. 6A, a distal end of the puller wire 48 is anchored near the distal end of the deflection section 14 by a T-bar 55 as known in the art. Along the length of the lumen 15 of the catheter body 12, the puller wire is surrounded by a compression coil 57, as shown in FIG. 3A. The compression coil has a proximal end at or near a junction between the control handle 16 and the catheter body 12, and a distal end at or near the distal end of the catheter body 12. Accordingly, when the puller wire 48 is drawn proximally by manipulation of the deflection knob 13 (FIG. 1) on the control handle 16, the compression coil 57 stops compression along its length so that the puller wire 48 deflects the deflection section 14 distal of the catheter body 12. The catheter may include a second puller wire for bi-directional deflection, as known in the art.

A distal electromagnetic location sensor 42D is connected to sensor cable 36D that extends through the lumen 224 of selected cabling 210' (FIG. 3B) which extends from the catheter body 12 and control handle 16 and out the proximal end of the control handle 16 (FIG. 1) within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 36D comprises multiple wires encased within a plastic covered sheath. In the sensor control module, the wires of the sensor cable are connected to the circuit board. The circuit board amplifies the signal received from the corresponding location sensor and transmits it to a computer in a form understandable by the computer by means of the sensor connector at the proximal end of the sensor control module. Also, because the catheter is designed for single use only, the circuit board may contain an EPROM chip that shuts down the circuit board approximately twenty-four hours after the catheter has been used. This prevents the catheter, or at least the location sensor, from being used twice.

In one embodiment, the location sensor 42D comprises a magnetic-field-responsive coil, as described in U.S. Pat. No. 5,391,199, or a plurality of such coils, as described in International Publication WO 96/05758. The plurality of coils enables six-dimensional position and orientation coordinates to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. In one embodiment, an electromagnetic mapping sensor has a length of from about 3 mm to about 7 mm, preferably about 4 mm.

A proximal EM location sensor 42P may be provided at the proximal end of the assembly 18, as shown in broken lines in FIG. 6A. The sensor 42P is housed in the outer tubing 34 and a cable 36P, also shown in broken lines in FIG. 6A, for the proximal location sensor 42P may extend through the central lumen 15 of the catheter body 12, and the lumen 32 of the deflection section 14. With a second location sensor, the coordinates of the distal sensor 42D, relative to those of the proximal sensor 42P, are determined and taken together with other known information pertaining to the curvature of the spines 27 of the basket-shaped mapping assembly 18. This information is used to find the positions of the ring electrodes 240 mounted on the spines 26.

As would be recognized by one skilled in the art, other arrangements for constructing the proximal and distal junctions and for mounting the location sensors could also be used in accordance with the invention.

To use the catheter of the invention, an electrophysiologist introduces a dilator and a guiding sheath into the patient, as is generally known in the art. A suitable guiding sheath for use in connection with the inventive catheter is the PREFACE™ Braided Guiding Sheath (commercially available from Biosense Webster, Inc., Diamond Bar, Calif.). The catheter is introduced through the guiding sheath with the expander extended and the assembly collapsed so that the assembly can be fed into the guiding sheath. The guiding sheath covers the spines of the assembly in a collapsed position so that the entire catheter can be passed through the patient's vasculature to the desired location. Once the assembly of the catheter reaches the desired location, e.g., the left atrium, the guiding sheath is withdrawn to expose the assembly. The expander is drawn proximally or otherwise manipulated so that the spines flex outwardly. With the assembly radially expanded, the ring electrodes contact atrial tissue. Using the ring electrodes on the spines in combination with the location sensor(s), the electrophysiologist can map local activation time and/or ablate and irrigate as needed, in diagnosing and providing therapy to the patient. With the multiple electrodes on the assembly, the catheter enables the electrophysiologist to obtain a true anatomy of a cavernous region of the heart, including an atrium, by measuring more points than with traditional catheters, allowing him to map the region more quickly. Moreover, for focal tissue contact, the electrophysiologist can direct the distal tip with high density microelectrodes for greater location precision and greater sensitivity in detecting more subtle electrical activity of heart tissue.

Where better tissue contact is desired between the electrodes on the assembly 18 and/or the distal tip electrode 22, an axial force FD may be applied by the EP professional, as shown in FIG. 4A, wherein the spines 27 are sufficiently rigid in their distal and proximal regions 27D and 27P to ensure tissue contact while the flexible region 27E readily deforms to absorb and dampen any excessive force that may cause damage to tissue at the distal end of the assembly 18. Similarly, where the assembly 18 is advanced and encounters anatomy at its distal end, the risk of tissue damage by the distal tip electrode 22 is minimized by the flexible region 27E readily deforming to absorb and dampen excessive compressive force FP.

Figure 13A:
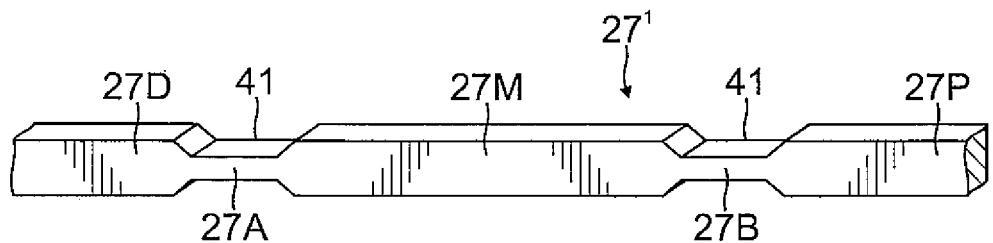
FIG. 13A is a perspective view of a spine with multiple portions of greater flexibility, in accordance with an embodiment of the present invention.
Figure 13B:
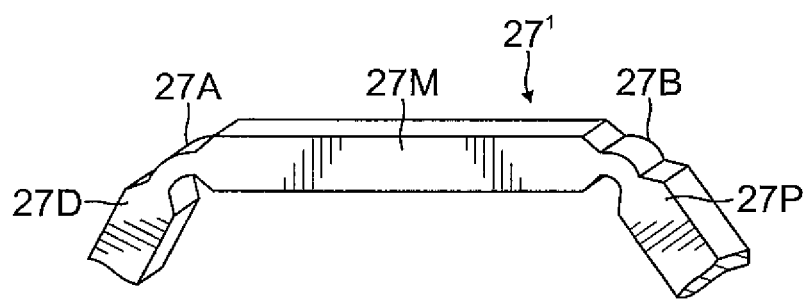
FIG. 13B is a perspective view of the spine of FIG. 13A, in a hyper-flexed configuration.
Figure 13C:
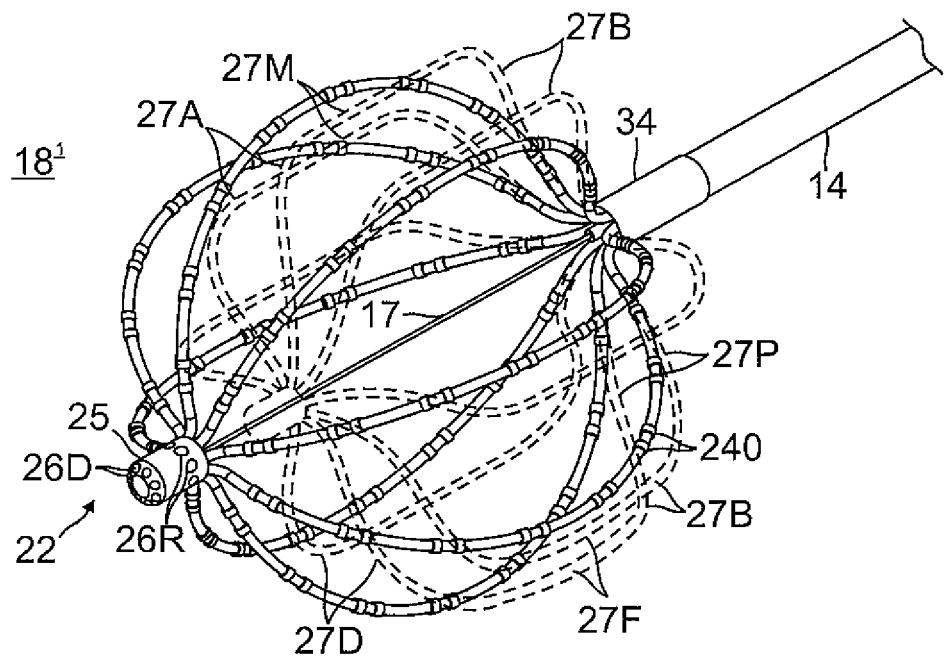
FIG. 13C is a perspective view of a basket-shaped electrode assembly with spines having multiple portions of greater flexibility, in accordance with an embodiment of the present invention.
Figure 13D:
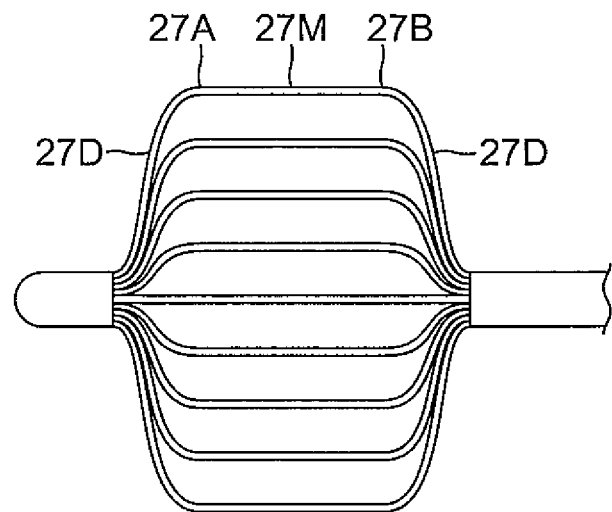
FIG. 13D is a side elevational view of the basket-shaped electrode assembly of FIG. 13C, in a hyper-flexed configuration.

FIGS. 13A and 13B illustrate another embodiment of the present invention, wherein at least one spine 27' of an assembly 18' has more than one region of greater flexibility spanning between regions of lesser flexibility by comparison. In the illustrated embodiment of FIG. 13A, a first region of greater flexibility 27A spans between the distal portion 27D and a mid-portion 27M, and a second region of greater flexibility 27B spans between the mid-portion 27M and the proximal portion 27P. Accordingly, the first and second regions of greater or hyper flexibility 27A and 27B readily deform and bend to form greater or acute bends so that the assembly 18' is compressed longitudinally to absorb a force acting on the assembly from either its distal end or its proximal end, as shown in FIG. 13C. When compressed, the spines 27' generally deform into a U-shape with the assembly 18 deforming more into a generally cylindrical shape, as shown in FIG. 13D, wherein the assembly is compressed longitudinally with the distal, mid and proximal portions 27D, 27M and 27M experiencing minimal deformation. Advantageously, the regions of greater flexibility in the spines allow the spine to readily elastically change between a first configuration with a generally uniform flexed curvature along its length to a second configuration having a generally uniform curvature at the distal, mid and proximal regions separated by regions with a hyper or more acute curvature.

In accordance with another feature of the present invention which may be incorporated in addition to or lieu of one or more other features of the present invention, the spines of the basket-shaped electrode assembly may be constructed with suitable materials, for example, Nitinol alloys with different As and/or Af, wherein As is the temperature where material starts to transform to austenite upon heating and Af is the temperature where material has finished transforming to austenite upon heating. In the illustrated embodiment of FIG. 4B, distal and proximal regions 27D and 27P include a first Nitinol alloy with a higher "As," and at least one region 27E includes a second Nitinol alloy with a lower "As." Accordingly, the first Nitinol alloy at the distal and proximal regions 27D and 27P begins to exhibits superelastic behavior at a higher temperature upon heating, and the second Nitinol alloy begins to exhibits superelastic behavior at a lower temperature upon heating. In another embodiment, the first Nitinol alloy may have a lower Af and the second Nitinol alloy may have a higher Af, such that the distal and proximal regions 27D and 27P have a higher temperature at which they have finished transforming to austenite upon heating, and the at least one region 27E has a lower temperature at which it has finished transforming to austenite upon heating. With reference to the embodiment of FIG. 13D, the distal, proximal and mid regions 27D, 27P and 27M may be constructed of the first Nitinol alloy and the regions 27A and 27B of greater flexibility may constructed of the second Nitinol alloy.

Figure 14A:
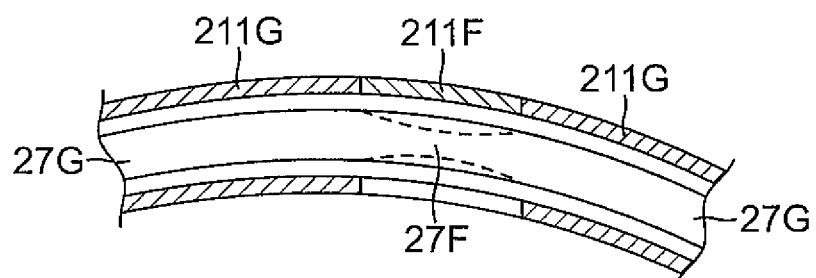
FIG. 14A is a side cross-sectional view of a spine with covering, in accordance with an embodiment of the present invention.
Figure 14B:
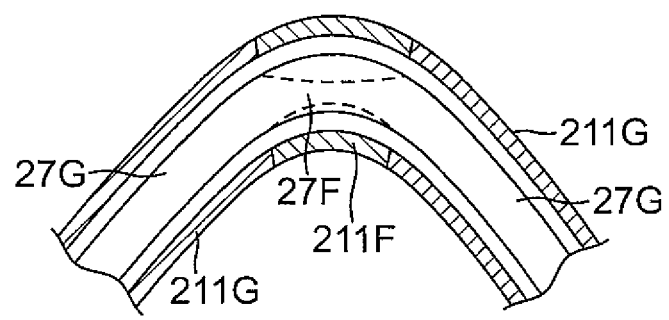
FIG. 14B is a side cross-sectional view of the spine of FIG. 14A, in a hyper-flexed configuration.

In accordance with another feature of the present invention which may be incorporated in addition to or lieu of one or more other features of the present invention, the spines are surrounded by nonconductive, protective covering or cabling 211 which include regions of different durometer or flexibility, as shown in FIGS. 14A and 14B. For example, the covering 211 includes at least one region 211F of greater (or hyper) flexibility (or lower durometer) and at least one region of lesser flexibility 27G. Moreover, the one region of greater flexibility 211F may generally align with a spine region of greater (or hyper flexibility) 27F (which may have a smaller cross section as shown in broken lines), and the one region of lesser flexibility (or higher durometer) 211G may generally align with a spine region of lesser flexibility (27F), such that the regions of spine and covering facilitate each other in flexing.

Figure 15A:
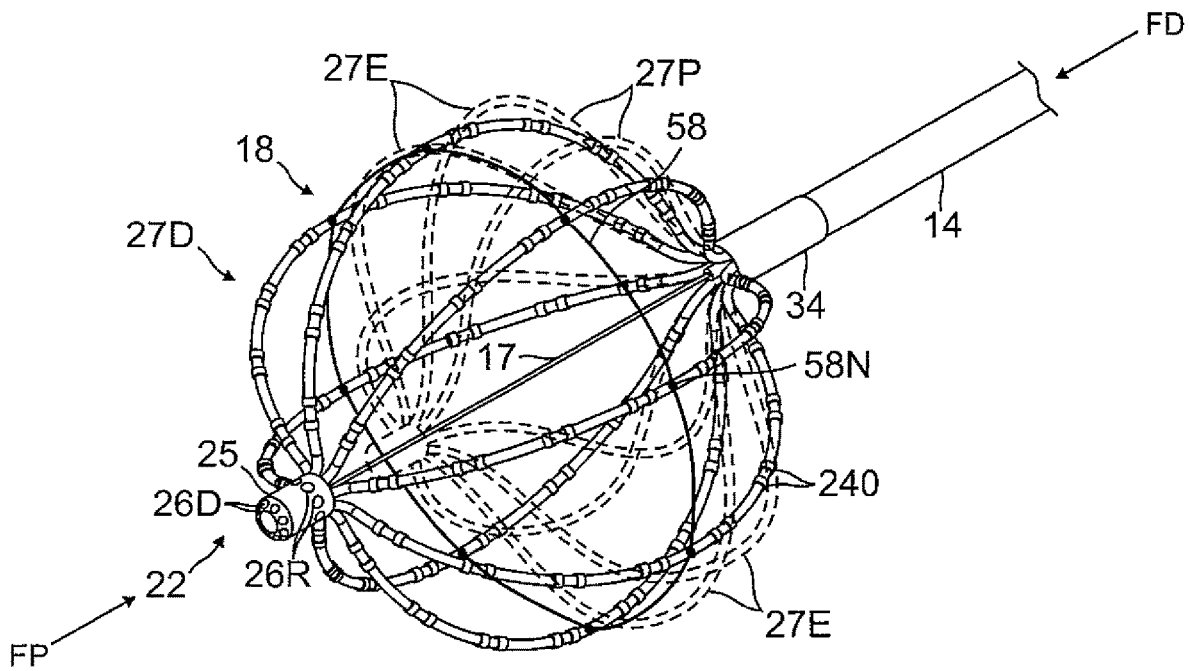
FIG. 15A is a detailed view of a basket-shaped electrode assembly, in accordance with another embodiment, in an expanded, deployed configuration.
Figure 15B:
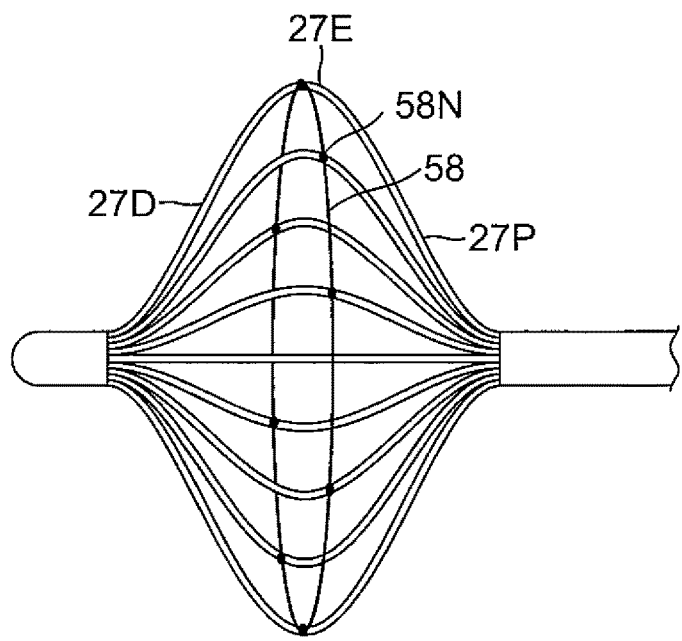
FIG. 15B is a perspective view of the assembly of FIG. 15A, in a hyper-flexed configuration.

In accordance with another feature of the present invention, the spines 27 are connected, tied or tethered to each other. With reference to FIGS. 15A and 15B, adjacent spines 27 are connected to each other by a tensile member 58 that is affixed to the spines 27 generally at their equatorial region or at the region of greater flexibility. The tensile member 48 helps to maintain spine and electrode spacing. The tensile member 58 may comprises individual sections whose ends are affixed to two adjacent spines, respectively, or it may have a continuous length affixed to each spine with a knot 58N. The tensile member 58 may be elastic or nonelastic, provided the length(s) are sufficient to accommodate the expanded and hyper-expanded configurations of the assembly.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale and any feature or combinations of features described in one embodiment may be incorporated into any other embodiments or combined with any other feature(s) of another embodiment, as desired or needed. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated catheter body having proximal and distal ends and at least one lumen therethrough; and
   a basket-shaped electrode assembly at the distal end of the catheter body, the basket-shaped electrode assembly having proximal and distal ends and comprising a generally cylindrical body having proximal and distal ends, the generally cylindrical body comprising:
     a proximal stem portion at the proximal end of the generally cylindrical body, and
     a plurality of spines extending from the proximal stem portion of the generally cylindrical body, at least one of the spines having an equatorial region of greater flexibility and proximal and distal regions of lesser flexibility, the basket-shaped electrode assembly being moveable between a collapsed configuration, an expanded configuration in which the spines bow radially outward relative to the catheter body to form a first expanded shape, and a hyper-expanded configuration in which the spines bend at the equatorial region of greater flexibility to thereby deform the first expanded shape, shorten a length of the basket-shaped electrode assembly and assume a V shape with an acute bend in the equatorial region of greater flexibility.

2. The catheter of claim 1, wherein the generally cylindrical body further comprises a distal stem portion, the plurality of spines extending between the proximal stem portion and the distal stem portion.

3. The catheter of claim 1, wherein each of the plurality of spines has a generally rectangular cross-section.

4. The catheter of claim 1, wherein the equatorial region of the at least one of the spines has a different and/or smaller cross-section than the proximal and distal regions.

5. The catheter of claim 1, wherein the at least one of the spines has a width dimension and a thickness dimension, and the equatorial region of greater flexibility has a lesser width and/or a lesser thickness than the first and second regions.

6. The catheter of claim 5, wherein the equatorial region of greater flexibility has a lesser width imparted by one or more indented regions or lateral notches.

7. The catheter of claim 6, wherein the one or more indented regions or lateral notches have a continuous contour or a stepped contour.

8. The catheter of claim 5, wherein the equatorial region of greater flexibility has a lesser thickness imparted by one or more inner and/or outer notches.

9. The catheter of claim 8, wherein the one or more inner and/or outer notches have a continuous contour or a stepped contour.

10. The catheter of claim 5, wherein the equatorial region of greater flexibility has a waist region imparting both a lesser width and a lesser thickness.

11. The catheter of claim 10, wherein the waist region has a continuous contour or a stepped contour.

12. A catheter comprising:
    an elongated catheter body having proximal and distal ends and at least one lumen therethrough; and
    a basket-shaped electrode assembly at the distal end of the catheter body, the basket-shaped electrode assembly having proximal and distal ends and comprising a generally cylindrical body having proximal and distal ends, the generally cylindrical body comprising:
      a proximal stem portion at the proximal end of the generally cylindrical body, and
      a plurality of spines extending from the proximal stem portion of the generally cylindrical body, at least one of the spines having first and second regions of greater flexibility and a mid region of lesser flexibility between the first and second regions of greater flexibility, the basket-shaped electrode assembly being movable between a collapsed configuration, an expanded configuration in which the spines bow radially outward relative to the catheter body to form a first expanded shape, and a hyper-expanded configuration in which the spines bend at the first and second regions of greater flexibility to thereby deform the first expanded shape and assume a U shape with first and second acute bends in the first and second regions of greater flexibility.

13. The catheter of claim 12, wherein the generally cylindrical body further comprises a distal stem portion, the plurality of spines extending between the proximal stem portion and the distal stem portion.

14. The catheter of claim 12, wherein the at least one of the spines has a width dimension and a thickness dimension, and the first and second regions of greater flexibility each independently has a lesser width and/or a lesser thickness than the mid region.

15. The catheter of claim 14, wherein the first and second regions of greater flexibility each independently has a lesser width imparted by one or more indented regions or lateral notches.

16. The catheter of claim 15, wherein the one or more indented regions or lateral notches have a continuous contour or a stepped contour.

17. The catheter of claim 14, wherein the first and second regions of greater flexibility each independently has a lesser thickness imparted by one or more inner and/or outer notches.

18. The catheter of claim 17, wherein the one or more inner and/or outer notches have a continuous contour or a stepped contour.

19. The catheter of claim 14, wherein the first and second regions of greater flexibility each independently has a waist region imparting both a lesser width and a lesser thickness.

20. The catheter of claim 19, wherein the waist region has a continuous contour or a stepped contour.

* * * * *